(12) United States Patent
Milbocker et al.

(10) Patent No.: US 11,963,684 B2
(45) Date of Patent: Apr. 23, 2024

(54) MICROSTRUCTURED HEMOSTAT

(71) Applicant: BVW Holding AG, Cham (CH)

(72) Inventors: Michael Milbocker, Holliston, MA (US); Lukas Bluecher, Eurasberg (DE)

(73) Assignee: BVW Holding AG, Cham (CH)

( * ) Notice: Subject to any disclaimer, the term of this patent is extended or adjusted under 35 U.S.C. 154(b) by 754 days.

(21) Appl. No.: 16/823,009

(22) Filed: Mar. 18, 2020

(65) Prior Publication Data
US 2021/0290241 A1   Sep. 23, 2021

(51) Int. Cl.
*A61F 13/00* (2006.01)
*A61B 17/12* (2006.01)
*A61L 31/04* (2006.01)

(52) U.S. Cl.
CPC .. *A61B 17/12009* (2013.01); *A61F 13/00021* (2013.01); *A61L 31/042* (2013.01); *A61L 31/044* (2013.01); *A61B 2017/12004* (2013.01); *A61L 2300/418* (2013.01)

(58) Field of Classification Search
None
See application file for complete search history.

(56) References Cited

U.S. PATENT DOCUMENTS

| | | |
|---|---|---|
| 9,120,670 B2 | 9/2015 | Hulseman et al. |
| 9,908,274 B2 | 3/2018 | Hulseman et al. |
| 9,988,201 B2 | 6/2018 | Darin et al. |
| 10,377,044 B2 | 8/2019 | Hulseman et al. |
| 10,458,053 B2 | 10/2019 | Hulseman et al. |
| 10,575,667 B2 | 3/2020 | Hulseman et al. |
| 10,687,642 B2 | 6/2020 | Hulseman et al. |
| 10,889,005 B2 | 1/2021 | Hulseman et al. |
| 2012/0107851 A1 | 5/2012 | Killard et al. |
| 2015/0368838 A1 | 12/2015 | Hulseman et al. |
| 2017/0014111 A1 | 1/2017 | Hulseman et al. |
| 2019/0062155 A1 | 2/2019 | Hulseman et al. |
| 2019/0117849 A1 | 4/2019 | Bluecher et al. |
| 2020/0338808 A1 | 10/2020 | Hulseman et al. |
| 2021/0086371 A1 | 3/2021 | Hulseman et al. |

FOREIGN PATENT DOCUMENTS

| | | | |
|---|---|---|---|
| DE | 4426315 C1 * | 3/1996 | ........... A61F 13/023 |
| EP | 573275 A2 | 12/1993 | |

OTHER PUBLICATIONS

DE 4426315 C1 English translation. (Year: 1996).*
Search Report and Written Opinion for corresponding patent application No. PCT/US2021/022589, dated Jun. 21, 2021, 15 pages.
Brown M R et al: "Fractal discrimination of random fractal aggregates and its application in biomarker analysis for blood coagulation" Chaos, Solitons and Fractals, vol. 45, No. 8, 23, Apr. 23, 2012, pp. 1025-1032.

* cited by examiner

*Primary Examiner* — Kim M Lewis
(74) *Attorney, Agent, or Firm* — Patterson Intellectual Property Law, P.C.; Ryan D. Levy; Mark A. Kilgore

(57) ABSTRACT

A microstructured hemostat comprising multiple layers of microstructure, each layer characterized by one or more length scales, is described. Microstructured hemostats of the present invention, can reduce the time for blood coagulation, control the morphology of the coagulation, and provide a novel diagnostic platform for evaluation of coagulation function from a morphological perspective.

15 Claims, 5 Drawing Sheets

MICROSTRUCTURED HEMOSTAT

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application claims benefit of the following patent application(s) which is/are hereby incorporated by reference: None

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND SUMMARY

The present disclosure relates generally to devices and methods useful in perioperative cessation of bleeding, correction of coagulation defects by promoting prescribed clot morphology, and as diagnostic surfaces useful in the evaluation of coagulation morphology. Such devices and methods are useful in surgical procedures, preventing post-surgical adhesions, maintaining a patent lumen, and quantifying coagulation pathologies. Additionally, such hemostatic devices are useful in the local reversal of a pharmaceutically-induced coagulation deficiency. More particularly, this disclosure pertains to multifunctional hierarchical microstructures and three-dimensional anchored interfacial domain structures that result in super-slippery and super-adhesive devices.

Coagulation pathway changes play an important role in the outcome of clot propagation. The structure-function relationship of the developing fibrin clot is known to be affected by many factors, such as environment, therapy, and disease, compared with normal clot growth. In some cases, an environmental factor can compensate for a deficiency due to a disease factor.

A fibrin clot primary microstructure consists of a disordered network of entangled, branching fibrin fibers. Thinner fibers are associated with networks that display an increased number of branch points, creating denser, less permeable clots that have a known association with thromboembolic disease. This observation suggests that microstructured surfaces can play a role in guiding the structure of the clot by matching hierarchical structure of the hemostat/implant to a desired branching ratio of the fibrin fibers.

Clots with altered fibrin microstructure exhibit different susceptibility to fibrinolysis, with clot permeability being the rate-limiting factor for the activity of the fibrin network degradation enzyme plasmin.

An arterial stent, patterned appropriately, may alter the permeability of a clot, if it were to form, which may aid or hamper the ability of tissue plasmin activator, and/or urokinase plasmin activator to move through the 3-dimensional fibrin network and activate the zymogen plasminogen to fibrinolytic plasmin.

It is known that the clotting of blood involves formation of fractal and hierarchical domains of solid and liquid. It has now been discovered that these domains correspond to differences in surface energy that occur repeatedly on many size scales in a self-similar way. Additionally, it has been unexpectedly found that a solid surface patterned with alternating high energy and low energy regions, arranged hierarchically, can significantly enhance and/or reduce clotting time by anticipating the natural clotting microstructure.

What is needed then is a microstructured surface to overcome the problem of rapidly stopping blood flow from a defect created in living tissue.

Further, there is a growing need to provide a functional biomarker in terms of a "healthy index" for normal clotting, from which the effect of therapeutic manipulation and disease on clot quality and outcome can be monitored.

BRIEF SUMMARY

The current disclosure provides in one embodiment a device for promoting blood coagulation. The device may include a hierarchically arranged microstructured surface that is configured to have a fractal dimension of between 2 and 3, and wherein the microstructured surface is configured to promote thrombus formation when in contact with blood. In some embodiments, the device may include a fractal dimension between 2.06 and 2.08. And in yet other embodiments, the device may include a fractal dimension of 2.07.

In one embodiment, the device may include a hierarchically arranged microstructured surface that includes at least a first surface texture and a second surface texture. Due to the hierarchical arrangement, the second surface texture may be disposed on the first surface texture. Further, the at least two surface textures may be configured to create a plurality of spatially distributed surface energy gradients.

In one embodiment, the hierarchically arranged microstructured surface further comprises a third surface texture, the third surface texture being hierarchically arranged on the second surface texture. In addition, the first surface texture may be arranged in a triangular grid and include a height of at least 400 microns. The second surface texture may be 25 microns in diameter and 45 microns in height. And the third surface texture may be 5 microns in diameter and 15 microns in height. In one embodiment, the second surface texture and third surface texture may also each be arranged in a triangular grid, similar to the first surface texture.

In one embodiment, the third surface texture may further include a vertical surface that is fluted, and wherein each flute may have a width of 5 microns.

In some embodiments, the hierarchically arranged microstructured surface is configured to have an activated partial thromboplastin time that is reduced relative to a surface that lacks a hierarchical microstructure arrangement.

In some embodiments, a device for separating blood components may include a hierarchically arranged microstructured surface wherein the hierarchically arranged microstructured surface may include a first distinct surface and a second distinct surface. The first and second distinct surfaces may each have a center, wherein the center for the first distinct surface may be located at least 50 microns from the center of the second distinct surface. The first distinct surface may be configured to localize a first blood component comprising substantially solids and the second distinct surface may be configured to localize a second blood component comprising substantially fluids.

In one embodiment, the first distinct surface may include at least two microstructured textures which are hierarchically arranged. The first distinct surface having a first fractal dimension. The second distinct surface may include at least two microstructured textures which are hierarchically arranged, the second distinct surface having a second fractal dimension. In some embodiments, the second distinct surface may be configured to remove the second blood component via capillary action.

In one embodiment, the first distinct surface and second distinct surface may cooperate such that the hierarchically arranged microstructured surface may have an activated partial thromboplastin time that is reduced relative to a surface that lacks a hierarchical microstructure arrangement.

In some embodiments, a device for promoting blood coagulation may include a surface, which may have a hierarchical microstructure and a chemical coagulant. The chemical coagulant may be cross-linked to the microstructure.

In some embodiments, the chemical coagulant may include *Gardenia* fruit extract, free amino groups of collagen/gelatin, and/or at least one oxidized polysaccharide. In some embodiments, the surface may comprise a polymer substrate containing at least one aldehyde group.

DETAILED DESCRIPTION

Figure 1:
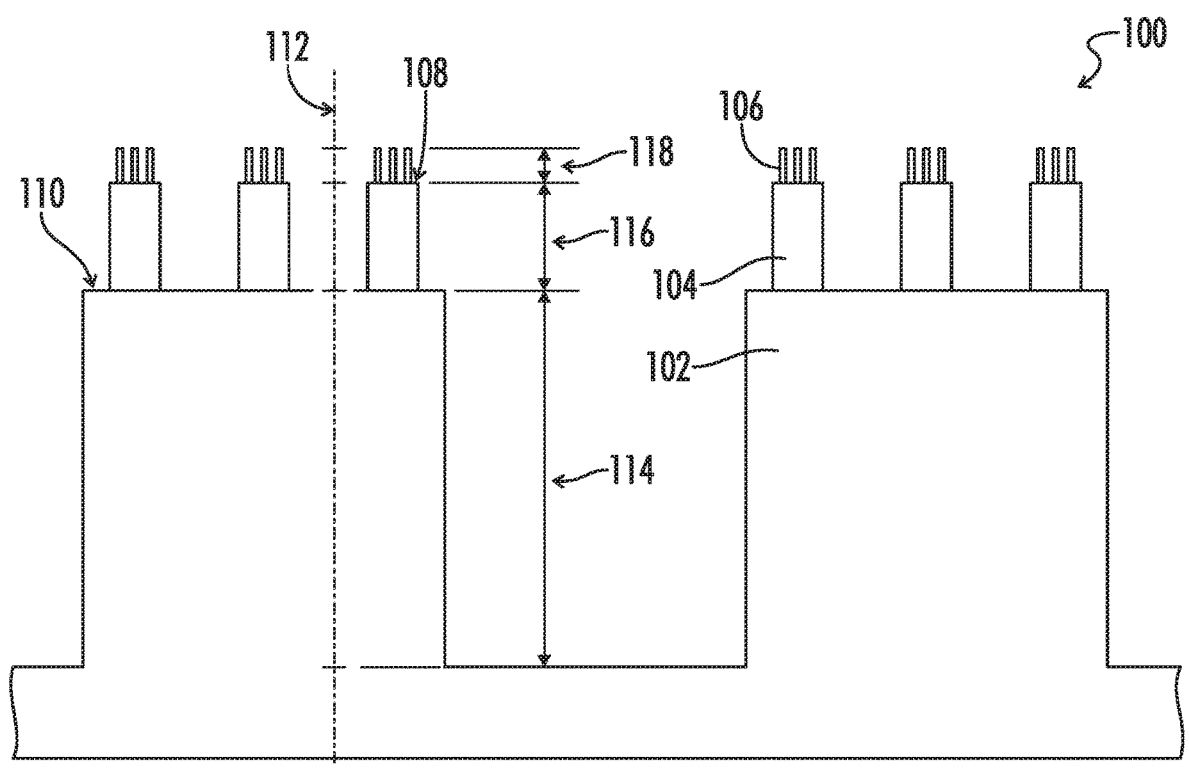
FIG. 1 is an embodiment of a hierarchically arranged microstructured surface.

Reference will now be made in detail to embodiments of the present disclosure, one or more drawings of which are set forth herein. Each drawing is provided by way of explanation of the present disclosure and is not a limitation. In fact, it will be apparent to those skilled in the art that various modifications can be made to the teachings of the present disclosure without departing from the scope of the disclosure. For instance, features illustrated or described as part of one embodiment can be used with another embodiment to yield a still further embodiment.

Thus, it is intended that the present disclosure cover such modifications and variations as come within the scope of the appended claims and their equivalents. Other objects, features, and aspects of the present disclosure are disclosed in, or are obvious from, the following detailed description. It is to be understood that one of ordinary skill in the art that the present discussion is a description of exemplary embodiments only and is not intended as limiting the broader aspects of the present disclosure.

As used herein, the term "microscopic" will be understood to include features of small enough dimension so as to require an optic aid to the naked eye when viewed from any plane of view to determine its shape. Normal visual acuity is considered to be when the smallest recognizable letter subtends an angular height of 5 minutes of arc on the retina. At a typical working distance of 250 mm (approx. 10 inches), this yields a lateral dimension of 0.36 mm (approx. 0.0145 inch) for this object.

As used herein, the term "microstructure" will be understood to include the configuration of features wherein at least 2 dimensions of the features are microscopic. As an example, the topological and cross-sectional view of the feature may be microscopic.

As used herein, the term "dimensional feature" will be understood to include features projecting out of the body of a microstructure surface with a specific range of sizes. For example, a dimensional feature of pillars with radius 10-20 microns and height 30-40 microns is distinguished from another dimensional feature of pillars with radius 80-100 microns and height 80-125 microns. Generally, the volumes of dimensional features are different by a factor of 10 or more.

As used herein, the term "positive features" will be understood to include features projecting out of the body of the microstructured molding tool, microstructured liner, microstructured backing, or microstructured pressure-sensitive adhesive layer.

As used herein, the term "negative features" will be understood to include features projecting into the body of the microstructured molding tool, microstructured liner, microstructured backing, or microstructured pressure-sensitive adhesive layer.

As used herein, the term "suctional aspect" will be understood to include a negative feature that may be capable of generating capillary motion.

As used herein, the term "embossable" will be understood to include the ability of a substrate layer to have part of its surface raised in relief, and other parts of its surface lowered in relief, especially by mechanical means.

As used herein, the term "substrate layer" will be understood to include a smooth, flat, planar piece of a substance such as thermoplastic, or polymer, that can receive microstructures by embossment, molding, printing, and casting, and where the microstructures become integral to the substrate layer.

As used herein, the term "wetting" will be understood to include spreading out over and intimately contacting a surface with a fluid. Aqueous fluids on hydrophilic surfaces may be wetting.

As used herein, the term "dewetting" will be understood to include a fluid contracting from intimate contact with a surface. Aqueous fluids on hydrophobic surfaces may be dewetting.

As used herein, the term "multi-functional microstructure" will be understood to include liquid, solid, and/or gas domains that develop on a microstructured surface when the surface comes into contact with a target surface. These domains may lower the surface energy of the microstructured surface and the target surface at the interface between the two surfaces. The interface may be rendered adhesive by the formation of a lower energy interface which requires energy to be supplied to the interface in order to separate the two surfaces. The physical forces responsible for domain formation may include van der Waals forces, Casimir forces arising from quantum interactions with the zero-point field, intermolecular forces, London dispersion forces, Debye force, Keesom forces, and hydrogen bonding. Adhesive microstructure does not refer to any chemically reactive substance applied to a surface to make it grip a target surface.

As used herein, the term "permanently repositionable multi-functional microstructured surface" will be understood to include a repositionable microstructured surface for which the strength of adhesion to a given target substrate may not change substantially with time under application conditions.

As used herein, the term "temporarily repositionable multi-functional microstructured surface" will be understood to include those repositionable microstructured surfaces which build adhesion with time, pressure, or temperature. This phenomenon may sometimes be referred to as a "suction effect" wherein the interface between the microstructured adhesive and target surface may progressively thin and may increase the energy of disassociation.

As used herein, the term "energy of dissociation" will be understood to include the difference in the surface energies of the microstructure and target surfaces apart and joined in an interface. Energy of dissociation will be understood to be a quantitative measure of the degree of adhesion within this disclosure.

As used herein, the term "target substrate" will be understood to include a surface to which the pressure-sensitive microstructured adhesive may be applied for an intended purpose.

As used herein, the term "exclusion zone" will be understood to include a region between a surface and water wherein due to the hydrophilicity of the surface, either due to surface texture or chemical characteristics, water may thermodynamically exclude ions and molecules that are not water.

As used herein, the term "structured water" will be understood to include a state of water wherein the water molecules in solution take a transition hexagonal form, which may be reinforced and sustained by the surface energy and chemistry between water and a solid surface.

As used herein, the term "capillary action" (sometimes capillarity, capillary motion, capillary rise, capillary effect, or wicking) will be understood to include the ability of a liquid to flow in narrow spaces without the assistance of, or even in opposition to, external forces like gravity. As an example, the effect may be seen in the drawing up of liquids between the hair of a paintbrush, in a thin tube, in porous materials such as paper and plaster, in some non-porous materials such as sand and liquefied carbon fiber, or in a cell. It is understood to occur due to intermolecular forces between the liquid and surrounding solid surfaces. If the diameter of the tube is sufficiently small, then the combination of surface tension and adhesive forces between the liquid and container wall may act to propel the liquid.

As used herein, the term "pitch" will be understood to include the center-to-center distance between two adjacent microstructures.

Generally, devices of the present application are microstructured hierarchically, meaning the microfeatures may be defined by distinct collections of feature sizes. For example, pillars may include a diameter of approximately 1-5 microns and may be arranged on the top surface of another set of pillars having a diameter of approximately 25-50 microns. This configuration may be referred to as complex pillars (multiple pillar sets arranged hierarchically) and may be arranged on a capillary bed comprising troughs with a capillary function.

It has been determined that these microstructured hierarchical surfaces may present domains of hydrophobicity (low surface energy) and domains of hydrophilicity (high surface energy) in close proximity, or juxtaposition, such that a composite liquid interface may be caused to self-differentiate into hydrophilic and hydrophobic zones. These types of microstructure hierarchical surfaces may create Wenzel-Cassie zones, where one part of the zone may be hydrophilic (Wenzel) and the other part may be hydrophobic (Cassie). Wenzel-Cassie zones can be generalized to oil-based aqueous solutions, composite fluids comprising particulate and water, and/or air/liquid composite fluids.

Wenzel-Cassie zones on devices of the present application may be particularly useful in blood contacting applications. Cassie zones may create a high contact angle between blood and the device surface, whereas Wenzel zones may wick away hydrophilic components, such as water. In some embodiments, such as a blood contacting application, a drop of blood contacting the microstructured surface may undergo fluid pinning, wherein the red blood cells and other particulates may be concentrated in the blood volume and the plasma (Cassie zone), and aqueous components may be wicked away by capillary action (Wenzel zone).

The result of blood pinning and concentration by capillary action may concentrate the blood, making coagulation faster and denser in morphology. Macroscopically, the microstructure device can be seen to "suck down" on the bleeding surface, thus stopping blood flow. In some embodiments, the cessation of blood flow may be caused prior to actual coagulation. The degree of capillary action can be tailored to the bleeding flow rate, such that rapidly bleeding surfaces may be more aggressively pinned than lesser bleeding surfaces.

In some embodiments, hemostats of the present disclosure may be more blood pinning centrally and more plasma wicking peripherally. Such anisotropy may be achieved by changing the size and/or pitch of the microstructures, as well as affecting the surface energy of the surfaces by surface treatments such as plasma activation or coating with an ionic compound. Alternatively, an activated surface may be achieved by creation of a nanostructure of the substrate material. For example, the substrate surface may be abraded, chemically lysed, or degraded in some mechanical way, including the deposition of nanoparticulate.

Surface energy can also be locally adjusted by implantation of microelectrodes, which may then be charged by an external source to reversibly alter surface energy. Electrolytic compounds may be used such that when they conduct blood the compounds may cause a current to flow and a charge to accumulate on discrete surfaces.

In some embodiments, the size and pitch of microfeatures may be chosen to promote coagulation and/or thrombus formation. In one embodiment, coagulation may begin on the scale of 1 micron. These small-scale thrombi may then combine on a characteristic scale to form larger thrombi. This evolution across characteristic dimensions is characteristic of the coagulation cascade. By matching the hierarchical structure of the microstructured surface to the characteristic dimensions of the coagulation cascade, coagulation may be enhanced. It should be understood that coagulation may be considered as a phase transition from a disordered fluid state to an ordered fibrous solid state. Patterns of localized surface energies may catalyze the phase transition from liquid blood to solid thrombus.

For coagulation mechanisms which are altered by disease or pharmaceuticals, the characteristic coagulation dimensions may change for some embodiments. This morphological change in the coagulation dynamics can be expressed as a branching ratio, where a fiber of length and diameter preferentially bifurcates whereas another fiber of different length and/or diameter may be less likely to bifurcate. When fibers bifurcate, their geometry may become fractal. Here, fractal geometry refers to a geometry that is part-way between a 2-dimensional plane geometry and a 3-dimensional volume geometry. The denser the bifurcation, the closer the geometry is to a 2-dimensional plane.

Recognizing the morphological behavior of coagulation may enable one to design better hemostats, and to design hemostats which correct for a particular coagulation dynamic. Furthermore, an array of microtextured surfaces exposed to blood of a certain coagulation dynamic may make a coagulation phase transition on one patterned surface rather than the others. Observing the coagulation time on microstructured surfaces of different fractal dimension can provide a quantitative means for diagnosing a patient's coagulation state.

Therefore, the embodiments of the present disclosure can be grouped into three categories: 1) hemostats with a normal coagulation promoting fractal dimension, 2) hemostats which catalyze a compromised coagulation pathway with a different fractal dimension, and 3) diagnostic surfaces that measure the fractal dimension of the coagulation pathway. These embodiments may be combined with chemical coagulants for yet further embodiments.

The embodiments of the present disclosure may be further enhanced by recognizing that the microstructured surface may actively direct the morphology of the resulting thrombus. A thrombus of low branching ratio may be more diffuse, porous, and easily lysed. A thrombus of high branching ratio may be more dense, impervious to fluid penetration, and structurally sound. In embodiments where the microstructured surface is in contact with flowing blood, the microstructured surface may be comprised of a material which resists thrombus formation and promotes diffuse thrombus formation should a thrombus form. In this embodiment, the microstructured surface may resist thrombus formation and, if thrombus formation should occur, guide thrombus formation into an easily resorbed configuration. For example, the formation of a diffuse fibrin structure can promote endothelialization, which may then become strongly antithrombotic. Endothelial cells are known to release nitric oxide, which may block thrombus formation.

One embodiment of the present invention is a microstructured surface with a specified branching ratio. Referring to FIG. 1, a hierarchical microstructure surface 100 has a branching ratio defined by hierarchical microfeatures including large microfeatures 102, medium microfeatures 104, and small microfeatures 106. In some embodiments, individual large microfeatures 102 may include a pitch of 1000 microns center-to-center, individual medium microfeatures 104 may include a pitch of 100 microns center-to-center, and individual small microfeatures 106 may include a pitch of 10 microns center-to-center. Small microfeatures 106 may be disposed on the top surface 108 of medium microfeature 104. Medium microfeature 104 may be disposed on the top surface 110 of large microfeature 102. In some embodiments, a reference line 112 may define a branching ratio where the height 114 of the large microfeature is 10 times the height 116 of the medium microfeature 104, and the height 116 of the medium microfeature 104 is 10 times the height 118 of the small microfeature 108. The reference line 112 may define a fractal dimension of 2.1=2+ ratio of successive lengths, where 2 is the dimension of the surface without microstructures. The fractal dimension of normal coagulation is approximately 2.07.

Figure 2:
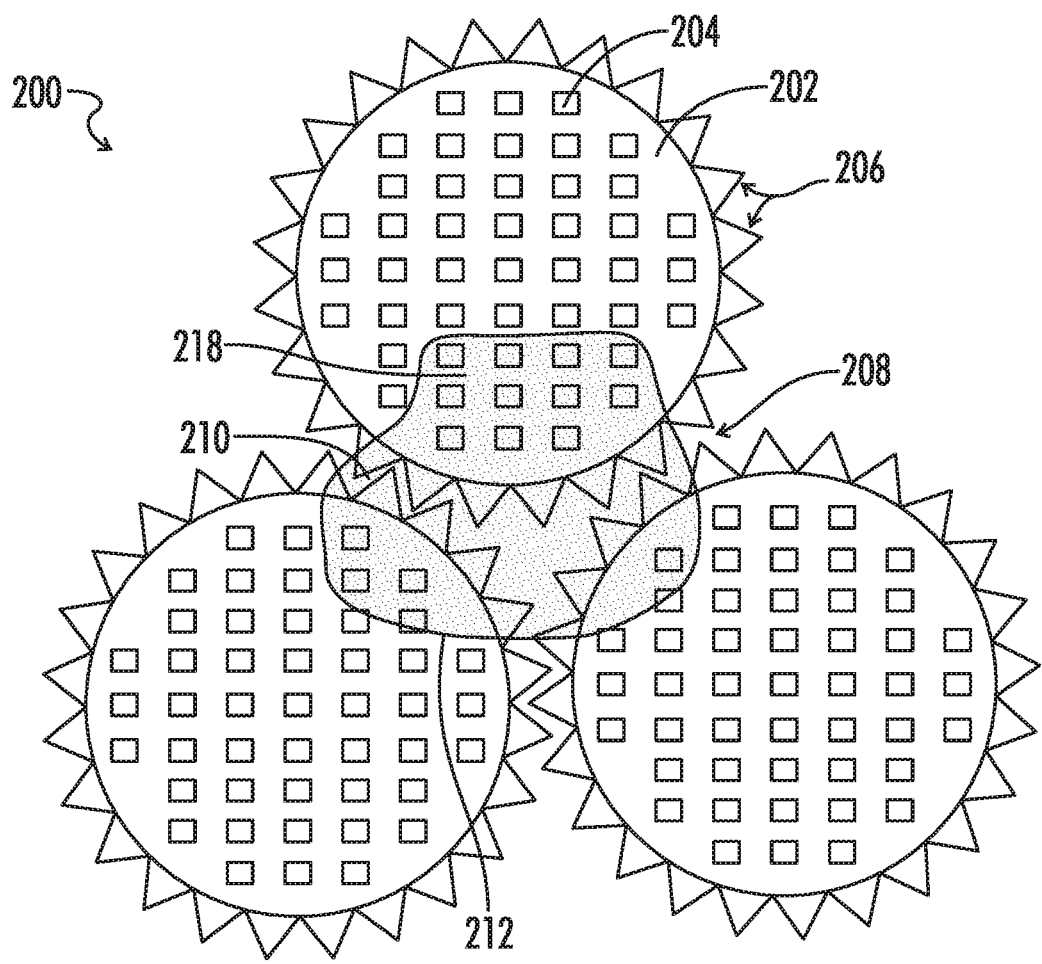
FIG. 2 is an embodiment of a hierarchically arranged microstructured surface with interpenetrating flutes.

It will be understood that in some embodiments, fractal dimension may not rely on microfeature shape. Instead of cylindrical pillars one could use square pillars, or any polygonal pillar. In embodiments with more angles disposed about the microfeature, the higher the surface energy of the microfeature may become. Microfeatures with fluted or finned side structures may be particularly useful in constructing Wenzel-Cassie structures. For example, referring to FIG. 2, a Wenzel-Cassie microstructure 200 is shown in top-view, and may be defined by large microfeatures 202 on the top of which are smaller microfeatures 204 arranged hierarchically. In some embodiments, the large microfeatures 202 may comprise flutes 206, wherein adjacent large microfeatures may have flues which are interpenetrating as illustrated in region 208. Due to the interpenetration of the flues, region 208 may be hydrophilic. Due to the hydrophilicity of this embodiment, fluid may be drawn down channel 210 via capillary action. Alternatively, in embodiments with smaller microfeatures 204 placed close together, for example at least 2 microns, the interpenetrating region 208 may be hydrophobic. Due to this configuration, a drop of blood 212 may be comprised of plasma and red blood cells and may be caused to concentrate the red blood cells to the top surface 218 of large microfeature 202, while the plasma may be drawn into channels 210, thus concentrating blood components, such as platelets, and compensating for a coagulation defect.

In some embodiments, a microstructure hemostat with Wenzel-Cassie microstructure 200 may stop active blood flow by causing the microstructure surface to be pulled in the direction of the tissue surface as plasma is wicked away from the interface surface. Alternatively, such patterns may be used to separate blood into liquid and solid components and isolate them with respect to each other.

Hemostats of the present disclosure may also be used in conjunction with chemical coagulants, such as fibrin-based sealant compositions, with and without collagen and/or an aldehyde-containing polymer. Crosslinking a fibrin-based sealant into a microstructured polymer having aldehyde groups may promote thrombin formation of an increased sealant strength.

In some embodiments, the fibrinogen component of the fibrin sealant may be derived from a cryoprecipitate concentrated by ultrafiltration. The fibrinogen component may include a fibrinogen content of from about 1-100 mg/ml, in particular from 50-75 mg/ml. The amount of fibrinogen may depend on the surface energies and surface energy gradients of the microstructures of the hierarchically arranged microstructured hemostat.

Cross links responsible for thrombus formation may be formed by Schiff base formation between free amino groups of the collagen/gelatin and aldehyde groups in the polymer. In some embodiments, the microstructured polymer may comprise polysaccharides. One example of a polysaccharide suitable for use in one embodiment is polymerized dextran. In another embodiment, an oxidized polymerized dextran or xanthan may be used.

The oxidized polysaccharides included in the present disclosure may preferably be an oxidized dextran in solution. However, other polysaccharides with suitable viscosity, molecular mass, and oxidation properties can also be used in various embodiments.

The molecular weight of the oxidized dextran used for the fabrication of wound dressings may be preferably below 5,000,000 daltons, more preferably between 10,000 and 100,000 daltons. In some embodiments, the viscosity of the aqueous solution of the dextran may be, for example, between 0.1 and 1 Pas for a 2% solution (as measured using a Brookfield LVT viscometer operated at 30 cycles).

Oxidation of dextran is a well-known reaction to one of skill in the art. For instance, oxidation may be conveniently obtained by treatment with an aqueous solution of a salt of periodic acid, such as sodium periodate. The purpose of the oxidation may be to create the formation of reactive dialdehyde residues on the microstructured surface of the polymer base.

Although the oxidation procedure described above may be used, it should be understood by one of skill in the art that other oxidation methods leading to the formation of dialdehyde residues may also possible in other embodiments. For instance, some embodiments for treatment with periodic acid or lead tetra acetate in an organic solvent such as dimethylsulfoxide may cause oxidation. After oxidation, the oxidized dextran may be conveniently purified and separated from low molecular weight reaction components by classical purification methods. Examples to accomplish this include, but are not limited to, precipitation (for instance by addition of acetone, methanol or isopropanol) or dialysis, ultrafiltration, or gel permeation chromatography, followed by lyophilisation.

Cross-linking between collagen or gelatin and oxidized dextran may be accomplished in-situ by the formation of so-called Schiff base links between free amino groups present on the collagen/gelatin (notably on the lysine residues thereof) and the dialdehyde residues on the oxidized dextran and the fibrinogen. These reactions may be catalyzed by the presence of high surface energy gradients.

In some embodiments, this reaction is initiated in the presence of blood, which may form an aqueous fibrin sealant medium and the speed and degree of cross-linking may depend on a variety of parameters. The parameters may include the type of collagen/gelatin, the concentration, the degree of dialdehyde substitution and molecular weight of the oxidized dextran, the pH, the buffer type, and/or the presence of electrolytes in the reaction medium.

In some embodiments, the percent coverage of the microstructure surfaces of the oxidized dextran may preferably be between 1% and 25%. In some embodiments, the concentrations of collagen/gelatin and oxidized dextran may be preferably between about 1% and about 25%, more preferably between 5 and 15%, even more preferably between 8 and 12%.

In some embodiments, the chemical coagulants may comprise one or more other substances to be deployed where platelets are concentrated within the microstructure of the microstructured hemostat. For example, they may comprise one or more substances that were present with the platelets. In some embodiments, the chemical additives can also comprise one or more salts, such as phosphate salts, sodium salts, potassium salts, calcium salts, magnesium salts, and any other salt, or any combination of two or more of these.

Other exemplary substances may be present in various embodiments of the microstructured surface including but not limited to sugars, such as monosaccharides and disaccharides (e.g., maltose, dextrose, mannose, trehalose, sucrose, polymers of sucrose, glucose); poly sugars, such as Ficoll-70 and Ficoll-400; glycerol; triglycerides; polysaccharides; lipids; dextran; polyvinyl pyrrolidone (PVP); starch; hydroxyethyl starch (HES); and the like.

Some embodiments may include biological molecules derived from human or animal sources, such as polypeptides (e.g., albumins such as bovine serum albumin and human serum albumin), casein, laminin, fibrinogen, and the like.

Some embodiments of microstructured hemostats of the present disclosure may include microstructures arranged hierarchically. This arrangement may concentrate platelet microparticles in addition to the platelets. In such embodiments, the concentrated platelets may comprise about 10% to about 60% of the total number of particles, particularly platelet or platelet-derived particles, in the composition. For example, platelets may comprise about 10% to about 50% of the particles, about 20% to about 50% of the particles, or about 30% to about 40% of the particles.

In other embodiments, about 70% of the platelet particles in the blood may be concentrated on a hierarchical surface where the blood retains particles of the size of a typical platelet. Thus, in some embodiments up to about 70% of the particles are concentrated platelets lying in a particular plane of the microstructured hemostat. Accordingly, the concentrated regions of the microstructured hemostat can comprise 70% platelets and 30% microparticles, 60% platelets and 40% microparticles, 50% platelets and 50% microparticles, 40% platelets and 60% microparticles, 20% platelets and 80% microparticles, or 10% platelets and 90% microparticles.

Of course, any particular specific whole number of platelets or microparticles within any of the ranges or amounts discussed above are contemplated by the disclosure. Because one of skill in the art would immediately recognize each of the numerous possible combinations of amounts of platelets and microparticles, it is not necessary to specifically disclose each herein.

The platelet concentrating region of the microstructured hemostat may be coated with a salt buffer that may include at least one saccharide, resulting in a buffered platelet-containing region. The salt buffer may be any buffer that maintains at least a majority of the platelets in an intact, functional state while in the buffer. The buffer may maintain the platelets at a pH of about 6 to 8, more preferably about 6.2 to about 7.8. The salt buffer may be an isotonic salt buffer comprising salts naturally encountered by platelets, such as those comprising sodium salts, potassium salts, calcium salts, and the like, and combinations of such salts.

In some embodiments, the microstructure surface may comprise one or more salts that platelets are not naturally in contact with. The identity of the salt(s) in the buffer should not be present in amounts that are toxic to the platelets and which cannot maintain at least a majority of the platelets in an intact, functional state while in the buffer. Likewise, the buffering component may be any buffer that is non-toxic to the platelets and provides adequate buffering capacity to the composition at the temperatures at which the composition will be exposed during the method of the disclosure.

The buffer may comprise any of the known biologically compatible buffers available commercially, such as HEPES, phosphate-buffered saline (PBS), and Tris-based buffers, such as TBS. Likewise, it may comprise one or more of the following buffers: propane-1,2,3-tricarboxylic (tricarbally-lic); benzenepentacarboxylic; maleic; 2,2-dimethylsuccinic; EDTA; 3,3-dimethylglutaric; bis(2-hydroxyethyl)imino-tris (hydroxymethyl)-methane (BIS-TRIS); benzenehexacarboxylic (mellitic); N-(2-acetamido)imino-diacetic acid (ADA); butane-1,2,3,4-tetracarboxylic; pyrophosphoric; 1,1-cyclopentanediacetic (3,3 tetramethylene-glutaric acid); 1,40 piperazinebis-(ethanesulfonic acid) (PIPES); N-(2-acetamido)-2-amnoethanesulfonic acid (ACES); 1,1-cyclohexanediacetic; 3,6-endomethylene-1,2,3,6-tetrahydrophthalic acid (EMTA; ENDCA); imidazole; 2-(aminoethyl) trimethylammonium chloride (CHOLAMINE); N,N-bis(2-hydroxyethyl)-2-aminoethanesulfonic acid (BES); 2-methylpropane-1,2,3-triscarboxylic (beta-methyltricarballylic); 2-(N-morpholino)propane-sulfonic acid (MOPS); phosphoric; N-tris(hydroxymethyl)methyl-2-amminoethane sulfonic acid (TES); and N-2-hydroxyethylpiperazine-N'-2-ethanesulfonic acid (HEPES). Furthermore, the buffer system can provide buffering capacity at the range of pH 4 to pH 8.

The following examples are meant to be illustrative but not limiting.

Example 1

Pattern A

Figure 3:
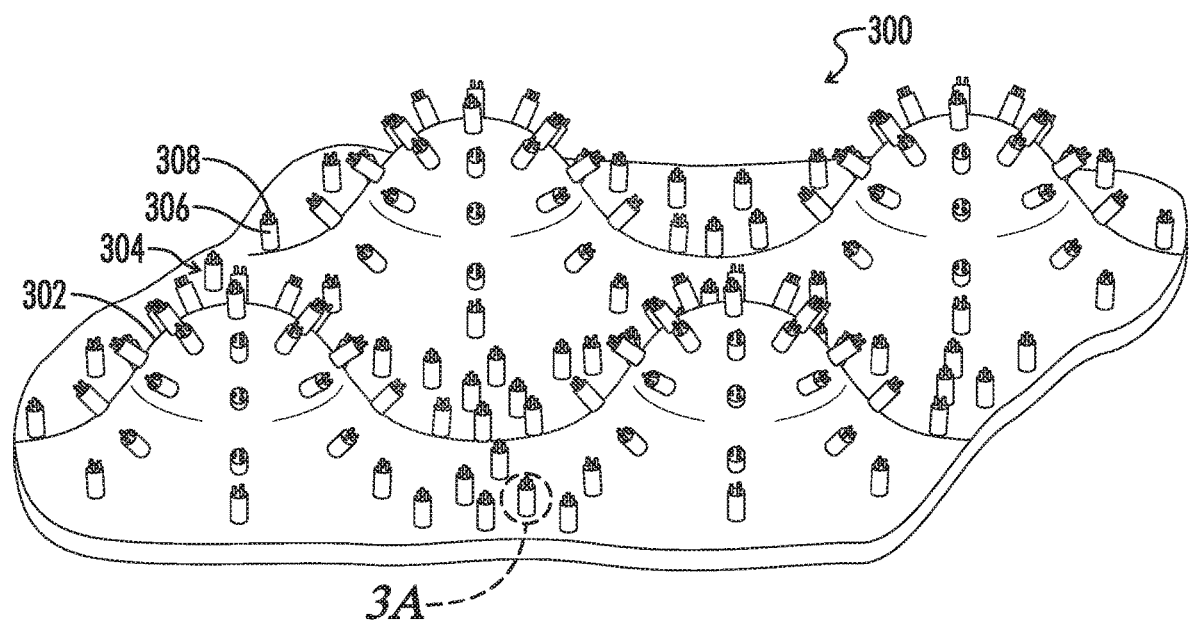
FIG. 3 is a perspective view of one embodiment of a hierarchically arranged microstructured surface of the present disclosure.
Figure 3A:
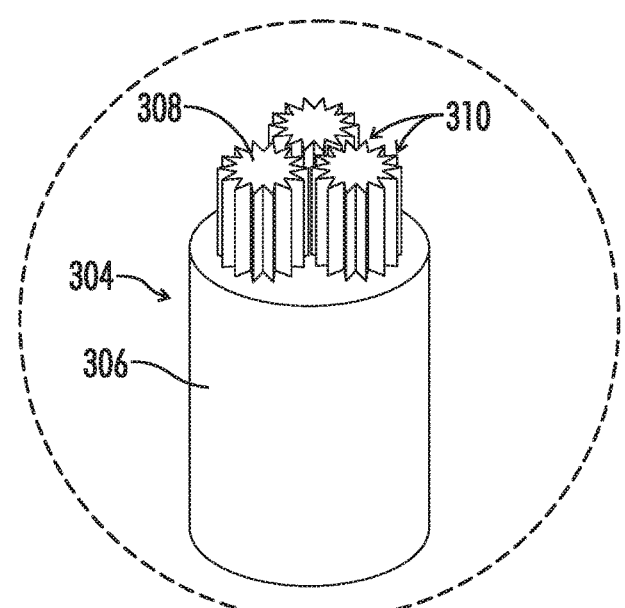
FIG. 3A is a larger perspective view of one microstructure as detailed in FIG. 3.

Referring to FIG. 3, a microstructured hemostatic surface 300 is shown and includes sinusoidal surface 302 and complex pillars 304. In some embodiments, the sinusoidal surface may be arranged to include a triangular grid. In some embodiments, the sinusoidal peaks may have a pitch of 1000 microns, measured from one peak to the adjacent peak, and wherein the sinusoidal peaks may include a peak height of 400 microns. The complex pillars 304 may be comprised of base pillars 306 and smaller pillars 308, and wherein the smaller pillars may include flutes 310 (see FIG. 3a). The base pillars 306 may be 25 microns in diameter and 45 microns in height. Additionally, the base pillars 306 may have a pitch of 75 microns measured from the center of one pillar to the center of an adjacent pillar and may be further arranged in a triangular grid. The smaller pillars 308 may be arranged in a triangular grid on the top surface of base pillar 306 wherein smaller pillars 308 may be 5 microns in diameter and 15 microns in height with a pitch of 15 microns. Flutes 310 may be triangular in cross section and may include a width and/or height of 5 microns.

Example 2

Pattern B

Figure 4:
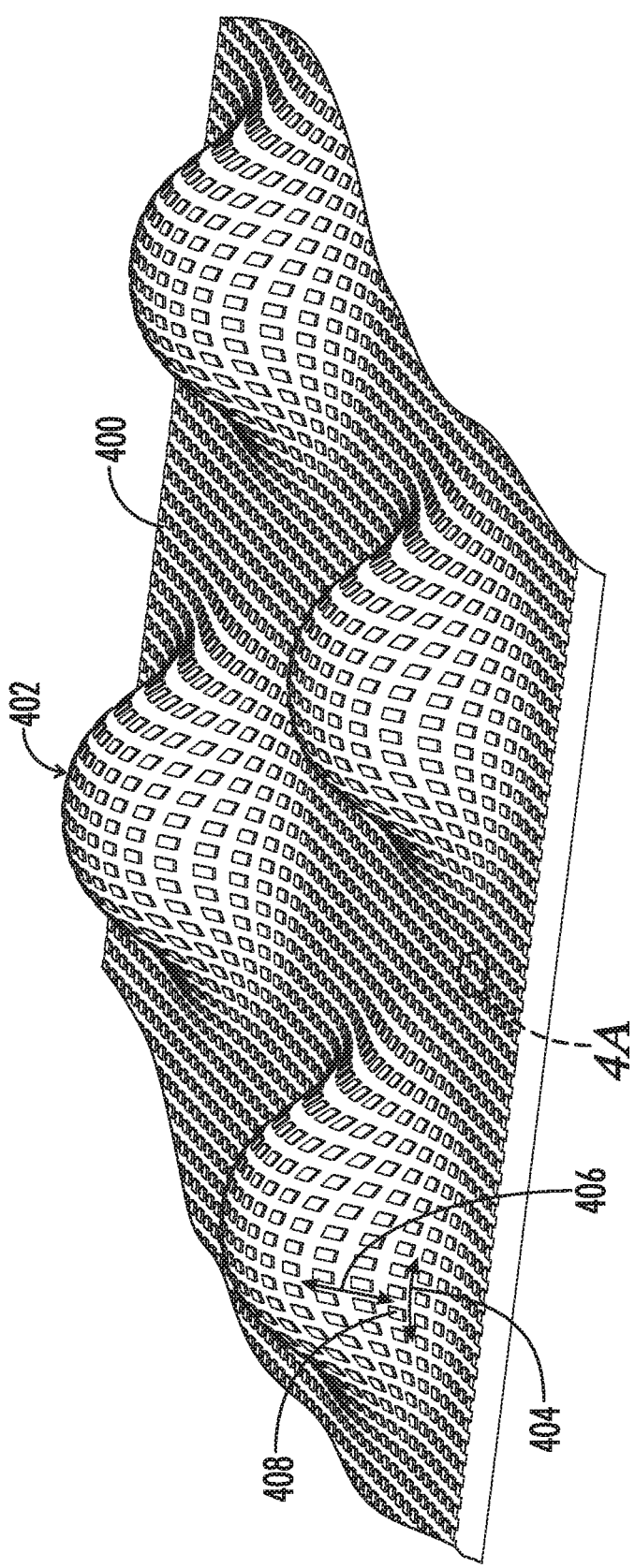
FIG. 4 is a perspective view of another embodiment of a hierarchically arranged microstructured surface of the present disclosure.
Figure 4A:
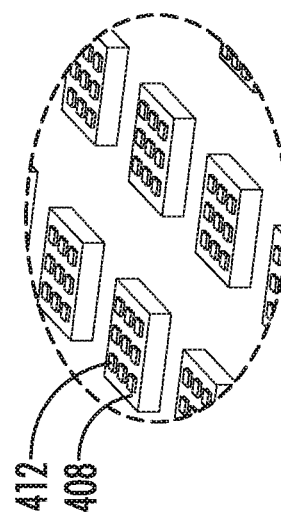

Referring to FIG. 4, a microstructured hemostatic surface 400 may include a sinusoid microstructure 402 which may include a height of 400 microns on a triangular grid with a pitch of 1000 microns. Superimposed on the hemostatic surface 400 may be longitudinal parallel grooves 404 and latitudinal parallel grooves 406, where grooves 404, 406 may be arranged orthogonally. In some embodiments, the grooves 404, 406 may have a width of 25 microns with a pitch of 50 microns from center-to-center. Longitudinal grooves 404 may include a depth of 50 microns in some embodiments. Latitudinal grooves 406 may include a depth of 100 microns in some embodiments. In some embodiments, the grooves 404, 406 may be configured such that the arrangement of the depths of each groove creates a pillar 408. In some embodiments, the pillar 408 may be square having 25 microns in length and width. In some embodiments, the top surface of pillars 408 may be machined to provide smaller pillars 412 disposed thereon. In some embodiments, the smaller pillars 412 may include a width of 5 microns and a pitch of 10 microns. In some embodiments, the smaller pillars 412 may be arranged in a square grid, triangular grid, or randomly.

Example 3

Demonstration of Microstructure Promoted Hemostasis

Purpose: The activated partial thromboplastin time (aPTT) is a test performed to investigate bleeding disorders and to monitor patients taking an anti-clotting drug such as heparin, which may inhibit factors X and thrombin, while activating anti-thrombin. The aPTT may be measured as a function of textured surface structure for embodiments as disclosed in Examples 1 and 2, above.

Heparin was added to determine if a microstructured hemostat can locally reverse the effects of Heparin (0.018 IU/100 cc blood).

Methods: Fresh bovine blood was obtained and decalcified to prevent clotting before the test began. Blood was collected in vials and decalcified by adding 0.01M citrate. The plasma was separated and set aside by centrifugation. At the time of testing, plasma was mixed with calcium ion to start the intrinsic pathway of the coagulation cascade. Kaolin (hydrated aluminum silicate) was added to activate the cascade. Kaolin activates contact-dependent Factor XII. The partial thromboplastin time is the time it takes for a clot to form, measured in seconds. Normally, the sample will clot in 35 seconds on a smooth glass surface.

Test Articles: (0.1 cc activated blood)
Embodiment of Example 1—polypropylene
Embodiment of Example 2—polypropylene Results: In comparing glass to microstructured surfaces, the process of clot formation appears to proceed with the formation of tiny islands of clots, which then join together to form the macroscopic clot.

Based on these results, larger clots without heparin were studied in a quiescent environment (rather than agitated). On the glass, normal blood coagulation appears to proceed through a series of solid phase formations that occur over several size scales. This is evidence of a fractal dimension operation, which generally may start at the 1-micron level. These islands join into 10-25 micron islands, which then fuse together on the 1000 micron scale.

In the case of heparinized blood, these islands do not form, rather the whole test volume gels without structure formation.

A microstructured surface with at least a portion of the structure including dimensions of 1000 microns, may assist organization of clots across the entire range of clotting scales.

| Heparinized Blood (agitated) Test Article (N = 5) | Clotting Time (s) |
|---|---|
| Glass | 122 +/− 12 s |
| Example 1 | 53 +/− 5 s |
| Example 2 | 81 +/− 8 |

Coagulation of normal blood on glass may evolve by a fractal dimension scaling law. Coagulation of heparinized blood may not scale in the same dimension, where the whole blood volume may gel at the same time. The result is an amorphous clot mass, rather than one that is fibrous.

Heparinized blood, agitated, yielded improved thromboplastin time on microstructured surfaces relative to glass. The coagulation morphology may return to the normal fractal dimension scaling law for heparinized blood when the coagulation is guided by hierarchical microstructure.

Example 4

Pattern C

Figure 5:
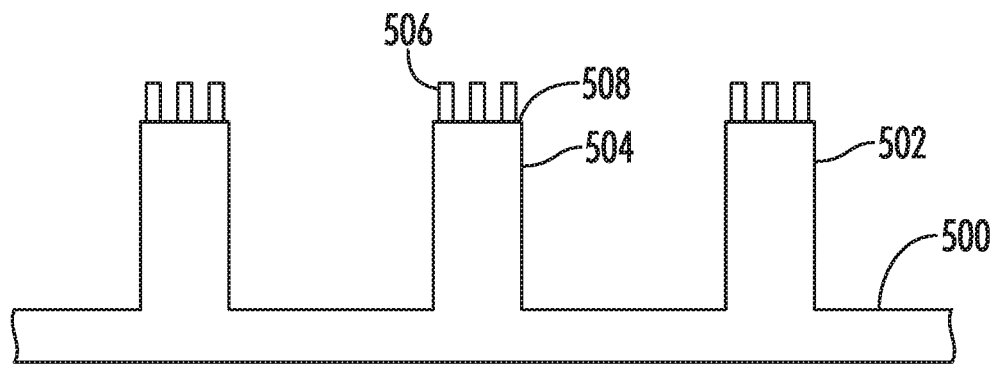
FIG. 5 is a side view of an embodiment of a hierarchically arranged microstructured surface of the present disclosure.

Referring to FIG. 5, a complex pillar surface 500 is comprised of complex pillars 502. The complex pillars 502 are comprised of base pillars 504 and smaller pillars 506. The base pillars 504 are arranged on a triangular grid and may include a pitch of 100 microns. The base pillars 504 may also have a diameter of 40 microns. The smaller pillars 506 may be hierarchically arranged on the top surface 508 of base pillars 504. The smaller pillars 506 may also be arranged in a triangular grid and have a pitch of 10 microns. The smaller pillars 506 may have a diameter of 5 microns.

Example 5

Demonstration of Microstructure Promoted Hemostasis

Purpose: The activated partial thromboplastin time (aPTT) is a test performed to investigate bleeding disorders and to monitor patients taking an anti-clotting drug such as heparin, which may inhibit factors X and thrombin, while activating anti-thrombin. The aPTT is measured as a function of textured surface and Gardenia fruit extract (a coagulant).

Methods: Fresh bovine blood was obtained and decalcified to prevent clotting before the test begins. Blood was collected in vials and decalcified by adding 0.01M citrate. The plasma was separated and set aside by centrifugation. At time of testing, plasma was mixed with calcium ion to start the intrinsic pathway of the coagulation cascade. Kaolin (hydrated aluminum silicate) was added to activate the cascade. Kaolin activates contact-dependent Factor XII. The partial thromboplastin time is the time it takes for a clot to form, measured in seconds. Normally, the sample will clot in 35 seconds on a smooth glass surface.

Test Articles: (0.1 cc activated plasma)

Glass plate with and without 1% w/w Gardenia extract; Example 1 embodiment with polypropylene with and without 1% w/w Gardenia extract; Example 4 embodiment with polypropylene with and without 1% w/w Gardenia extract.

Results:

| Test Article (N = 5) | Clotting Time (s) |
| --- | --- |
| Glass | 39 +/− 3 s |
| Glass + Gardenia | 25 +/− 5 s |
| Pattern A | 32 +/− 3 s |
| Pattern A + Gardenia | 19 +/− 2 s |
| Pattern C | 29 +/− 3 s |
| Pattern C + Gardenia | 14 +/− 2 s |

Example 6

A Compound Microstructured Hemostat

In some embodiments, a compound microstructured hemostat may be used to correct a coagulation deficiency by removing serum from a bleeding surface and concentrating platelets and red blood cells near the wound-device interface.

Figure 6:
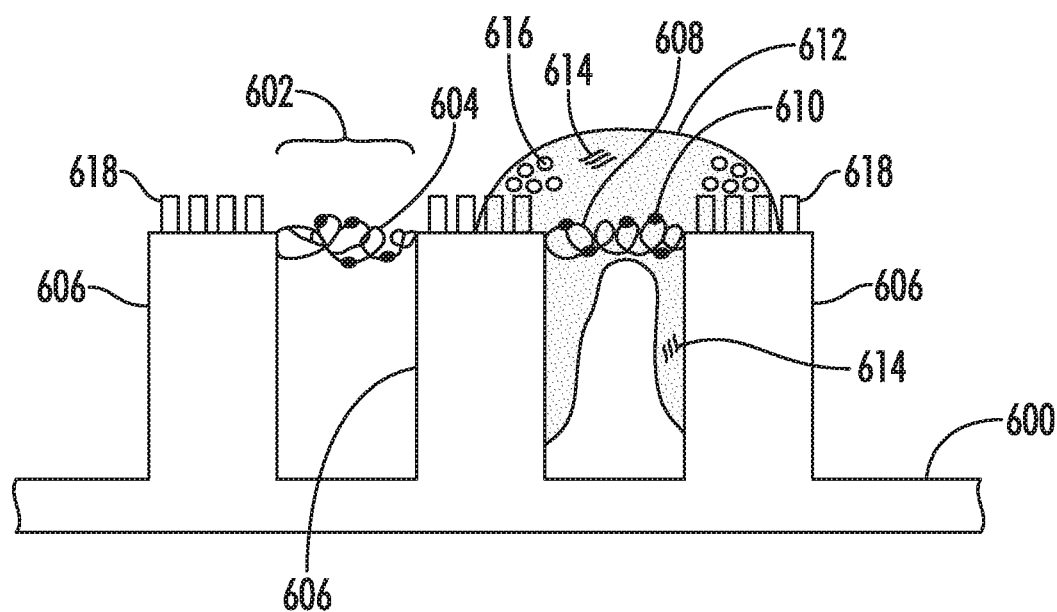
FIG. 6 is a side view of another embodiment of a hierarchically arranged microstructured surface of the present disclosure.

Referring to FIG. 6, a compound microstructured hemostat 600 is illustrated. The hemostat 600 may include a first component 602 which may be comprised of electrospun fibers 604. The electrospun fibers may be distributed uniformly over a second surface, which in some embodiments may be a modified Pattern C (Example 4) 606. The electrospun fibers may be comprised of an axial section 608 with a diameter of 5 microns and a beaded section 610 with a diameter of 30 microns. The electrospun component 602 may include a porosity of 1 to 2 microns. Preferably the electrospun fibers 602 may be comprised of hydrophilic polymer. In one embodiment, for example, electrospun fibers 602 may comprise an absorbable polyurethane.

In some embodiments, the microstructured hemostat 600 may be used such that a drop of blood 612 may be comprised of liquid serum 614 and solids 616 and come into contact with the microstructured hemostat 600. The solids 616 may include red blood cells, platelets, and/or microparticles. The first component 602 may have capillary contact with large pillars 606. Liquid serum 614 may be drawn between large pillars 606, and solid 616 may accumulate on small pillars 618. This arrangement may represent a Wenzel-Cassie interface which immobilizes the solids 616 in first component 602 and may promote thrombus formation. The liquid serum 614 may be drawn away from first component 604 and into second component 606.

The fluid component can be made to flow away from the thrombus formation continuously, due to distal evaporation over a considerably larger surface distal to the wound site. Optionally, one can create a capillary reservoir distal to the wound site for sequestration.

Example 7

Pattern D

In some embodiments, a compound microstructured hemostat may be used to decrease wound bleeding by decreasing the time for coagulation to occur. In one embodiment, this effect may be caused by removing serum from a bleeding surface and concentrating platelets and red blood cells near the wound-device interface.

In some embodiments, a hemostat device may include surface on which is disposed hierarchical microstructures. In one embodiment, the hierarchical microstructures may include a first pillar and a second pillar, wherein the second pillar is disposed about the first pillar. The first pillar may have a circular cross-section with a height of 200 microns, a diameter of 100 microns, and a pitch of 200 microns. The second pillar may have a circular cross-section with a height of 20 microns, a diameter of 10 microns, and a pitch of 20 microns. When this embodiment is applied to an incision or wound site where bleeding occurs, the bleeding is stopped at a faster rate than with a surface that has no hierarchical microstructures.

Example 8

Pattern E

In some embodiments, a microstructured hemostat may utilize an electrospun frame surrounding a microstructured surface. In one embodiment, the frame of the hemostat may include a 5-micron PET fiber which may be 500 microns thick. The frame may be disposed on a PLA backing. The PLA backing may include a hierarchical microstructure having a first pillar and a second pillar, and wherein the second pillar is disposed about the first pillar. The first pillar may have a circular cross-section with a height of 200 microns, a diameter of 100 microns, and a pitch of 200 microns. The second pillar may have a circular cross-section with a height of 20 microns, a diameter of 10 microns, and a pitch of 20 microns.

In some embodiments, an electrospun frame and microstructured device as disclosed above may contact blood and cause coagulation within approximately 2 minutes. Additionally, the blood may continue to flow through the microstructured layer and then contact the electrospun frame, causing the hemostat to be "sucked down" onto the target interface and cause coagulation in place. In some embodiments, the blow flow may be retrograde and caused to flow back through the incision hole or wound.

Thus, although there have been described particular embodiments of the present disclosure of a new and useful Microstructured Hemostat, it is not intended that such references be construed as limitations upon the scope of this disclosure except as set forth in the following claims.

What is claimed is:

1. A device for promoting blood coagulation comprising: a hierarchically arranged microstructured surface comprising at least a first surface texture and a second surface texture, the second surface texture being hierarchically disposed on the first surface texture, wherein the at least two surface textures are configured to create a plurality of spatially distributed surface energy gradients via Wenzel-Cassie wetting states, wherein a first portion of the microstructured surface generates Cassie wetting states, and a second portion of the microstructured surface generates Wenzel wetting states, the first portion of the microstructured surface having a higher contact angle than the second portion of the microstructured surface, wherein the hierarchical arranged microstructured surface is configured to have a fractal dimension of between 2 and 3, and wherein the microstructured surface is configured to promote thrombus formation when in contact with blood.

2. The device of claim 1 wherein the fractal dimension is between 2.06 and 2.08.

3. The device of claim 2 wherein the hierarchically arranged microstructured surface is configured to have an activated partial thromboplastin time that is reduced relative to a surface that lacks a hierarchical microstructure arrangement.

4. The device of claim 1 wherein the hierarchically arranged microstructured surface further comprises a third surface texture, the third surface texture being hierarchically arranged on the second surface texture, and wherein the first surface texture is arranged in a triangular grid and having a height of at least 400 microns, wherein the second surface texture is 25 microns in diameter and 45 microns in height, and wherein the third surface texture is 5 microns in diameter and 15 microns in height.

5. The device of claim 4, wherein the second surface texture and third surface texture are each arranged in a triangular grid.

6. The device of claim 4, wherein the third surface texture further comprises a vertical surface that is fluted, each flute having a width of 5 microns.

7. The device of claim 1, wherein the first portion of the microstructured surface having a higher contact angle generates fluid pinning and the second portion of the microstructured surface generates capillary action.

8. The device of claim 1, wherein the first surface texture comprises a plurality of microfeatures having a pitch between adjacent microfeatures of 100 microns, and the second surface texture comprise a plurality of microfeatures having a pitch between adjacent microfeatures of 10 microns.

9. The device of claim 1, wherein the microstructured surface further comprises a chemical coagulant.

10. The device of claim 9, where the chemical coagulant comprises fibrinogen.

11. The device of claim 1, wherein the microstructured surface is capable of concentrating about 70% of blood platelets on the hierarchical arranged microstructured surface.

12. The device of claim 1, wherein the first surface texture comprises at least one microfeature having a height of 200 microns, a diameter of 100 microns, and a pitch of 200 microns.

13. The device of claim 12, wherein the second surface texture comprises at least one microfeature having a height of 20 microns, a diameter of 10 microns, and a pitch of 20 microns.

14. The device of claim 1, wherein the device is a hemostat comprising a polylactic acid substrate having the microstructured surface.

15. The device of claim 14, wherein the device is capable of being in contact with blood and causing coagulation within about 2 minutes.

* * * * *